United States Patent
Kharashi et al.

(10) Patent No.: US 12,392,763 B2
(45) Date of Patent: Aug. 19, 2025

(54) HYDROCARBON CONTAMINANT DETECTION USING POLYMER FILM

(71) Applicants: Saudi Arabian Oil Company, Dhahran (SA); King Abdullah University of Science and Technology, Thuwal (SA)

(72) Inventors: Khawlah Kharashi, Thuwal (SA); Maha Nour, Thuwal (SA); Khaled Nabil Salama, Thuwal (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 310 days.

(21) Appl. No.: 18/135,535

(22) Filed: Apr. 17, 2023

(65) Prior Publication Data
US 2024/0345061 A1    Oct. 17, 2024

(51) Int. Cl.
*G01N 33/28*    (2006.01)

(52) U.S. Cl.
CPC ................ *G01N 33/2888* (2013.01)

(58) Field of Classification Search
CPC ... G01N 33/2888; G01N 33/2835; G01N 1/44
See application file for complete search history.

(56) References Cited

U.S. PATENT DOCUMENTS 4,434,233 A * 2/1984 Bzdula ............... G01N 27/06
                                                           436/60
2021/0389264 A1   12/2021 Ito et al.

2022/0155328 A1 *  5/2022 Sliz ..................... C12M 41/34
2024/0328980 A1 * 10/2024 Nour .................. G01N 27/128
2024/0329030 A1 * 10/2024 Nour .................. G01N 27/122
2024/0345026 A1   10/2024 Nour et al.
2024/0345060 A1   10/2024 Nour et al.
(Continued)

FOREIGN PATENT DOCUMENTS

CN        111504850 A  *  8/2020

OTHER PUBLICATIONS

Agha et al., "A Review of Cyclic Olefin Copolymer Applications in Microfluidics and Microdevices," Macromolecular Materials and Engineering, 2022, 307(2200053): 1-34, 35 pages.
(Continued)

*Primary Examiner* — Francis C Gray
(74) *Attorney, Agent, or Firm* — Fish & Richardson P.C.

(57) ABSTRACT

A hydrocarbon contaminant detection system using a polymer film includes a sensor assembly, a syringe and a controller. The sensor assembly includes a cyclic olefin copolymer (COC) film including electrically conductive materials. The sensor assembly can complete an electrical circuit. The COC film can dissolve in a presence of a hydrocarbon contaminant to cause the electrical circuit to break. The syringe can carry a lubrication oil sample to be tested using the sensor assembly. The syringe is operable to contact the lubrication oil sample with the COC film of the sensor assembly. The controller includes one or more processors, and a computer-readable medium storing instructions which when executed by the one or more processors cause the one or more processors to perform operations including operating the syringe to flow the lubrication oil sample onto the COC film of the sensor assembly at a pre-determined flowrate.

20 Claims, 5 Drawing Sheets

(56) References Cited

U.S. PATENT DOCUMENTS

2024/0345063 A1 10/2024 Kharashi et al.
2024/0345064 A1 10/2024 Nour et al.

OTHER PUBLICATIONS

COC Topas Product Brochure, Section 4.2; Table 2, Mar. 2006, 20 pages.

Ghosh et al., "A mass manufacturable thermoplastic based microfluidic droplet generator on cyclic olefin copolymer," J. Micromechanics Microengineering, Apr. 10, 2019, 29(5):055009, 9 pages.

Jain et al., "Design and Simulation of Microfluidic Passive Mixer With Geometric Variation," Int. J. Res. Eng. Technol., Feb. 2016, 5(2):55-58, 4 pages.

Jena et al., "Cyclic olefin copolymer based microfluidic devices for biochip applications: Ultraviolet surface grafting using 2-methacryloyloxyethyl phosphorylcholine," Biomicrofluidics, Mar. 2012, 6(1):012822-1-012822-12, 12 pages.

Jena et al., "Micro fabrication of cyclic olefin copolymer (COC) based microfluidic devices," Microsystem Technologies, Oct. 18, 2011, 18(2):159-166, 8 pages.

Kimmich et al., "Fault detection for modern Diesel engines using signal- and process model-based methods," Control Eng. Pract., Feb. 2005, 13(2):189-203, 15 pages.

Li et al., "Isoelectric focusing in cyclic olefin copolymer microfluidic channels coated by polyacrylamide using a UV photografting method," Electrophoresis, May 2005, 26(9):1800-1806, 7 pages.

McGann et al., "Lean fuel detection with nanosecond-gated laser-induced breakdown spectroscopy," Combustion and Flame, Feb. 2021, 224:209-218, 10 pages.

McGuire et al., "Detection of the aromatic molecule benzonitrile (c-C6H5CN) in the interstellar medium, " Science, Jan. 12, 2018, 359(6372):202-205, 4 pages.

Nunes et al., "Cyclic olefin polymers: emerging materials for lab-on-a-chip Applications, " Microfluid Nanofluid, Apr. 2010, 9:145-161, 17 pages.

Taghizadeh-Alisaraei et al., "Fault detection of injectors in diesel engines using vibration time-frequency analysis," Applied Acoustics, Jan. 1, 2019, 143:48-58, 11 pages.

\* cited by examiner

HYDROCARBON CONTAMINANT DETECTION USING POLYMER FILM

TECHNICAL FIELD

This disclosure relates to detecting hydrocarbon contaminants, e.g., diesel, in a petroleum product, e.g., lubrication oil.

BACKGROUND

Lubrication oil developed and used in the oil and gas industry is sometimes doped with contaminants, e.g., hydrocarbon fuel such as diesel. To detect such contaminants, fuel markers are used as additives. Fuel markers can be used to mark the overall produced product (i.e., the lubrication oil) to protect a comparatively smaller quantity of the product. Consequently, implementing fuel markers to detect contaminants can be an expensive solution. Moreover, the quantity of the fuel marker used as the additive is directly related to the target detection concentration.

SUMMARY

This disclosure describes technologies relating to hydrocarbon contaminant detection using polymer film.

Certain aspects of the subject matter described here can be implemented as a hydrocarbon contaminant detection system. The system includes a sensor assembly, a syringe and a controller. The sensor assembly includes a cyclic olefin copolymer (COC) film including electrically conductive materials. The sensor assembly can complete an electrical circuit. The COC film can dissolve in a presence of a hydrocarbon contaminant to cause the electrical circuit to break. The syringe can carry a lubrication oil sample to be tested using the sensor assembly. The syringe is operable to contact the lubrication oil sample with the COC film of the sensor assembly. The controller includes one or more processors, and a computer-readable medium storing instructions which when executed by the one or more processors cause the one or more processors to perform operations including operating the syringe to flow the lubrication oil sample onto the COC film of the sensor assembly at a pre-determined flowrate.

An aspect combinable with any other aspect includes the following features. A syringe pump is operatively coupled to and controllable by the controller. The syringe pump can receive the syringe and flow the lubrication oil sample in the syringe onto the COC film of the sensor assembly at the pre-determined flowrate.

An aspect combinable with any other aspect includes the following features. The pre-determined flowrate is between 50 microliters per minute and 3 milliliters per minute.

An aspect combinable with any other aspect includes the following features. The sensor assembly and the syringe are spatially arranged at a pre-determined height from which the lubrication oil sample drops vertically onto the COC film.

An aspect combinable with any other aspect includes the following features. The pre-determined height is between 1 centimeter and 15 centimeters.

An aspect combinable with any other aspect includes the following features. The sensor assembly includes a first substrate layer. The COC film is positioned on top of the first substrate layer. A second substrate layer is positioned on top of the COC film. The second substrate layer defines a through opening through which the syringe flows the lubrication oil sample onto the COC film between the first substrate layer and the second substrate layer.

An aspect combinable with any other aspect includes the following features. The electrically conductive materials include an electrically conductive honeycomb sheet metal positioned below the through opening defined by the second substrate layer.

An aspect combinable with any other aspect includes the following features. A surface area of the first substrate layer is greater than a surface area of the second substrate layer. The sensor assembly includes electrically conductive metal disposed on portions of the first substrate layer exposed after the second substrate layer is positioned on top of the COC film. The electrically conductive metal contacts the COC film.

An aspect combinable with any other aspect includes the following features. The sensor assembly includes a light emitting diode (LED) electrically connected to the COC film. The LED can stay on in an absence of the hydrocarbon contaminant and can turn off in a presence of the hydrocarbon contaminant.

Certain aspects of the subject matter described here can be implemented as a method. An electrical circuit is formed between a sensor assembly including a cyclic olefin copolymer (COC) film including electrically conductive materials and a light emitting diode (LED). The LED remains turned on when the electrical circuit is complete and turns off when the electrical circuit is broken. A lubrication oil sample is flowed at a pre-determined flow rate onto the COC film. After flowing the lubrication oil sample at the pre-determined flow rate onto the COC film, it is detected that the LED switches off, indicating a presence of a hydrocarbon contaminant in the lubrication oil sample.

An aspect combinable with any other aspect includes the following features. The sensor assembly is formed by positioning the COC film on top of a first substrate layer. A through opening is formed through a second substrate layer. The second substrate layer is positioned over the COC film sandwiching the COC film between the first substrate layer and the second substrate layer.

An aspect combinable with any other aspect includes the following features. The electrically conductive materials are sputtered on the COC film. To position the second substrate layer over the COC film, the electrically conductive materials are positioned under the through opening.

An aspect combinable with any other aspect includes the following features. To sputter the electrically conductive materials, an electrically conductive honeycomb sheet metal is positioned on the COC film.

An aspect combinable with any other aspect includes the following features. A surface area of the first substrate layer is greater than a surface area of the second substrate layer. Electrically conductive metal is disposed on portions of the first substrate layer exposed after the second substrate layer is positioned on top of the COC film such that the electrically conductive metal contacts the COC film.

An aspect combinable with any other aspect includes the following features. The electrically conductive metal is disposed on exposed corners of the first substrate layer.

An aspect combinable with any other aspect includes the following features. To flow the lubrication oil sample at the pre-determined flow rate onto the COC film, the lubrication oil sample is loaded into a syringe. The syringe is positioned directly above the through opening such that the lubrication oil sample drops vertically downward onto the COC film through the through opening.

An aspect combinable with any other aspect includes the following features. The pre-determined flowrate is between 50 microliters per minute and 3 milliliters per minute.

An aspect combinable with any other aspect includes the following features. The pre-determined height is between 1 centimeter and 15 centimeters.

An aspect combinable with any other aspect includes the following features. To flow the lubrication oil sample at the pre-determined flow rate, the syringe is loaded onto a syringe pump. The syringe pump is operated to flow the lubrication oil sample through the syringe at the pre-determined flow rate.

Certain aspects of the subject matter described here can be implemented as a hydrocarbon contaminant detection system. The system includes a sensor assembly including a cyclic olefin copolymer (COC) film including electrically conductive materials. The COC film is sandwiches between a first substrate layer and a second substrate layer with a through opening to access the COC film. Electrically conductive materials are sputtered on the COC film. The sensor assembly can complete an electrical circuit. The COC film can dissolve in a presence of a hydrocarbon contaminant to cause the electrical circuit to break. The system includes a syringe that can carry a lubrication oil sample to be tested using the sensor assembly. The syringe is operable to contact the lubrication oil sample with the COC film of the sensor assembly. The system includes a syringe pump that can receive the syringe carrying the lubrication oil sample. The syringe pump can drive the syringe to flow the lubrication oil sample onto the COC film of the sensor assembly at a pre-determined flow rate. A break in the electrical circuit responsive to the lubrication oil sample being flowed onto the COC film indicates a presence of a hydrocarbon contaminant in the lubrication oil sample.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure describes a hydrocarbon contaminant detection system that implements a sensor assembly that includes a thin film of a polymer. The polymer can be a cyclic olefin copolymer (COC) which dissolves, disintegrates or otherwise loses structural integrity in the presence of the hydrocarbon contaminant, e.g., diesel fuel or any contaminant that contains aromatic chains. [Inventors: is COC the only type of polymer or material that can be used? Can other types of materials be used to detect other types of contaminants?] A layer of metal or other electrical conductor is sputtered on a surface (e.g., on top) of the COC film. When the COC film with the electrical conductor layer is coupled to a light emitter (e.g., a light emitting diode (LED)) and a power source (e.g., a battery), an electrical circuit is completed causing the light emitter to emit light.

To test for the presence of contaminants in lubrication oil, a sample of the lubrication oil is placed on the surface of the COC film. If the sample contains contaminants (e.g., diesel or contaminants with aromatic chains), then the COC film dissolves or loses structural integrity upon reacting with the contaminants. Such loss of structural integrity causes the electrical conductor layer to be dispatched from the surface and causes the electrical circuit to break. Consequently, the light emitter turns off. In contrast, if the light emitter remains turned on, that indicates that the sample is contaminant free. [Inventors: does this paragraph completely and accurately describe the COC film sensor?]

In some implementations, the hydrocarbon contaminant detection system is implemented to optimize a rate at which the lubrication oil sample is contacted with the COC film. For example, the flow rate at which the lubrication oil sample is dropped onto the COC film is optimized to control and improve (i.e., expedite) a dissolution rate of the COC film. Doing so enhances the detection time of contaminants in the sample. Controlled dropping of the lubrication oil sample onto the COC film allows fresh solvent molecules of the contaminant to continuously be in contact with the polymer film causing the polymer film to dissolve faster.

In some implementations, the hydrocarbon contaminant detection system is implemented to optimize a temperature at which the lubrication oil sample is contacted with the COC polymer. For example, the lubrication oil sample is heated to an optimized temperature before being dropped onto the COC film to control and improve (i.e., expedite) a dissolution rate of the COC film. Doing so enhances the detection time of contaminants in the sample. Heating the sample to the pre-determined temperature allows increasing the kinetic energy of the fluid to enhance the rapid motion of the molecules, thereby increasing the dissolving rate.

In some implementations, the hydrocarbon contaminant detection system described here can combine optimizing the temperature to which the lubrication oil sample is heated and optimizing the flow rate at which the heated sample is dropped onto the COC film. Implementations of the subject matter described here can enhance sensitivity of the hydrocarbon contaminant detection system. For example, diesel with concentrations of less than 1% can be detected. Implementations of the subject matter described here can also reduce the waiting time to determine the presence of the hydrocarbon contaminant in the sample. [Inventors: please list additional advantages, if any.]

Figure 1:
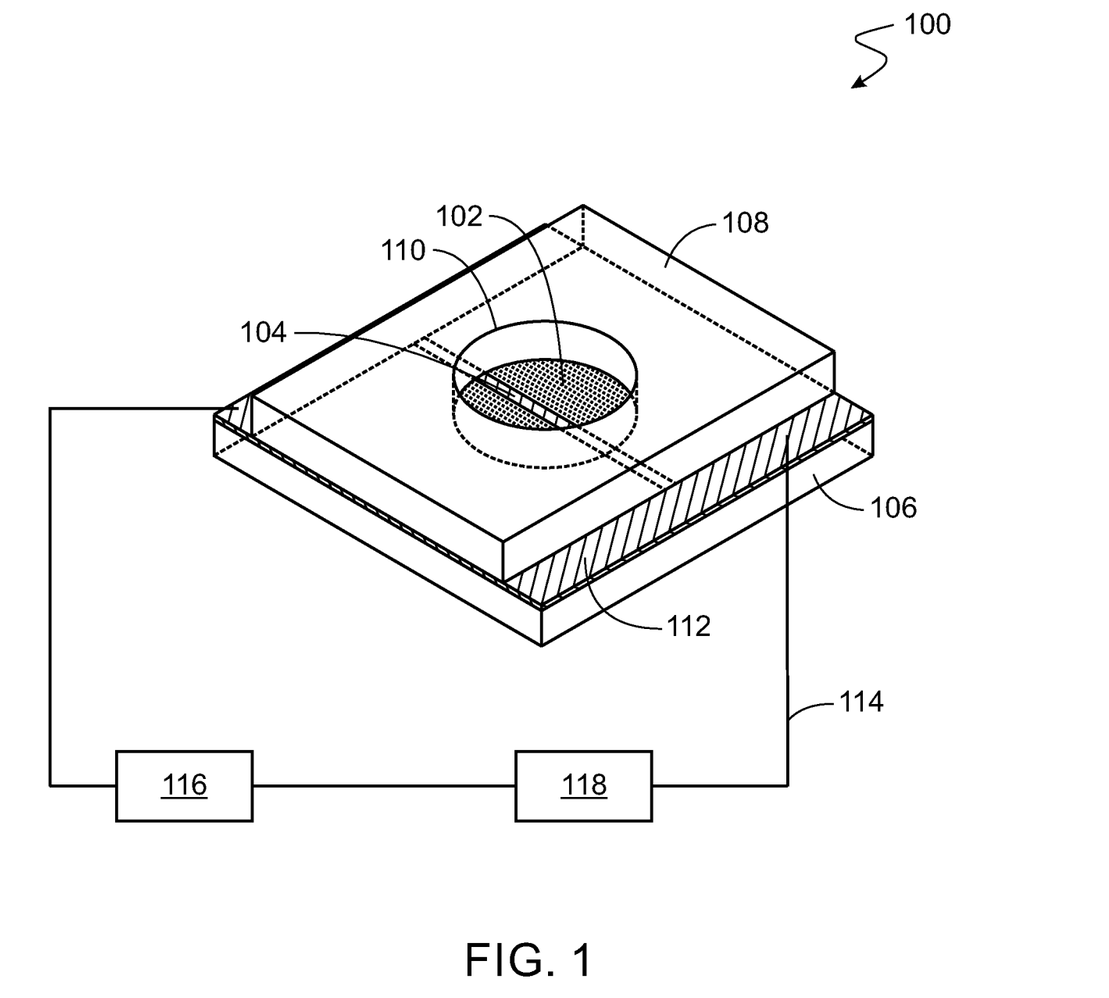
FIG. 1 is a schematic diagram of an example of a hydrocarbon contaminant detection system.

FIG. 1 is a schematic diagram of an example of a hydrocarbon contaminant detection system 100. The system 100 includes a sensor assembly which includes a cyclic olefin copolymer (COC) film 102 that can react in the presence of hydrocarbon contaminants (e.g., diesel) in a lubrication oil sample. As described earlier, the COC film 102 can lose structural integrity (e.g., dissolve or disintegrate) upon contacting the COC film 102. The COC film 102 includes electrically conductive materials 104 on a surface of the COC film 102. For example, the electrically conductive materials 104 can include a sheet metal sputtered like a honeycomb on the surface of the COC film 102. The electrically conductive materials 104 can form an interconnected layer on the COC film 102 that can conduct electricity from any edge to any other edge of the COC film 102.

The sensor assembly includes a first substrate layer 106 and a second substrate layer 108. Each substrate layer can be made of glass, polymethyl methacrylate (PMMA), silicon wafers or other electrically non-conductive material. The COC film 102 is positioned on the first substrate layer 106, and the second substrate layer 108 is positioned on the COC film 102. In this manner, the COC film 102 is sandwiched between the first and second substrate layers.

The second substrate layer 108 includes a through opening 110 formed, for example, at a geometric center of or offset from the center of the second substrate layer 108. The through opening 110 can be circular or of a different geometric shape.

In some implementations, the surface area of the first substrate layer 106 is greater than the surface area of the second substrate layer 108. For example, the first substrate layer 106 can be a larger rectangular prism than the second substrate layer 108. When the COC film 102 is sandwiched between the first and second substrate layers, surface area 112 near the edges of the first substrate layer 106 can be exposed. The exposed surface area can be coated with electrically conductive material, e.g., the same electrically conductive material 104 that is sputtered on the COC film 102.

Wires 114, i.e., electrical conducting wires, can be coupled to the electrically conductive material on the exposed surface area 112. The wires 114 can be connected to a power source 116 and to a light emitter 118 (e.g., an LED). Because the electrically conductive material on the exposed surface area 112 is in electrical contact with the electrically conductive material 104 sputtered on the COC film 102, an electrical circuit is completed, and the light emitter 118 is on in a default state of the system 100.

In some implementations, the surface area of the COC film 102 can be the same as the surface area of the first substrate layer 106. In such implementations, surface area of the COC film 102 can be exposed. The wires can be connected to the exposed areas of the COC film 102 to form the electrical circuit. In some implementations, to improve the electrical connection in the circuit, electrically conductive material can be disposed on the exposed surface area of the COC film 102 (e.g., on the corners of the COC film 102). The wires can be connected to the electrically conductive material disposed on the exposed surface area of the COC film 102.

To use the system 100, a quantity of lubrication oil sample is dropped onto the sensor assembly through the through opening 110. If the lubrication oil sample is contaminant free, i.e., free of the contaminant that can dissolve or disintegrate the COC film 102 of the sensor assembly, then the electrical circuit remains unbroken. The light emitter 118 remains in the default on state of the system 100. On the other hand, if the lubrication oil sample contains the contaminant that can dissolve or disintegrate the COC film 102 of the sensor assembly, then the electrical circuit breaks. The light emitter 118 turns off. A duration of time can pass from when the lubrication oil sample is dropped onto the sensor assembly through the through opening 110 and the light emitter 118 turns off (in the presence of the hydrocarbon contaminant). The duration depends on the time taken for the contaminant to dissolve or disintegrate the COC film 102. In addition, the concentration of the contaminant in the sample also affects the duration. For example, if the concentration is high, then the COC film 102 can dissolve/disintegrate faster. Conversely, if the concentration is low, then the COC film 102 can take longer to dissolve/disintegrate slower or may not dissolve/disintegrate.

Figure 2:
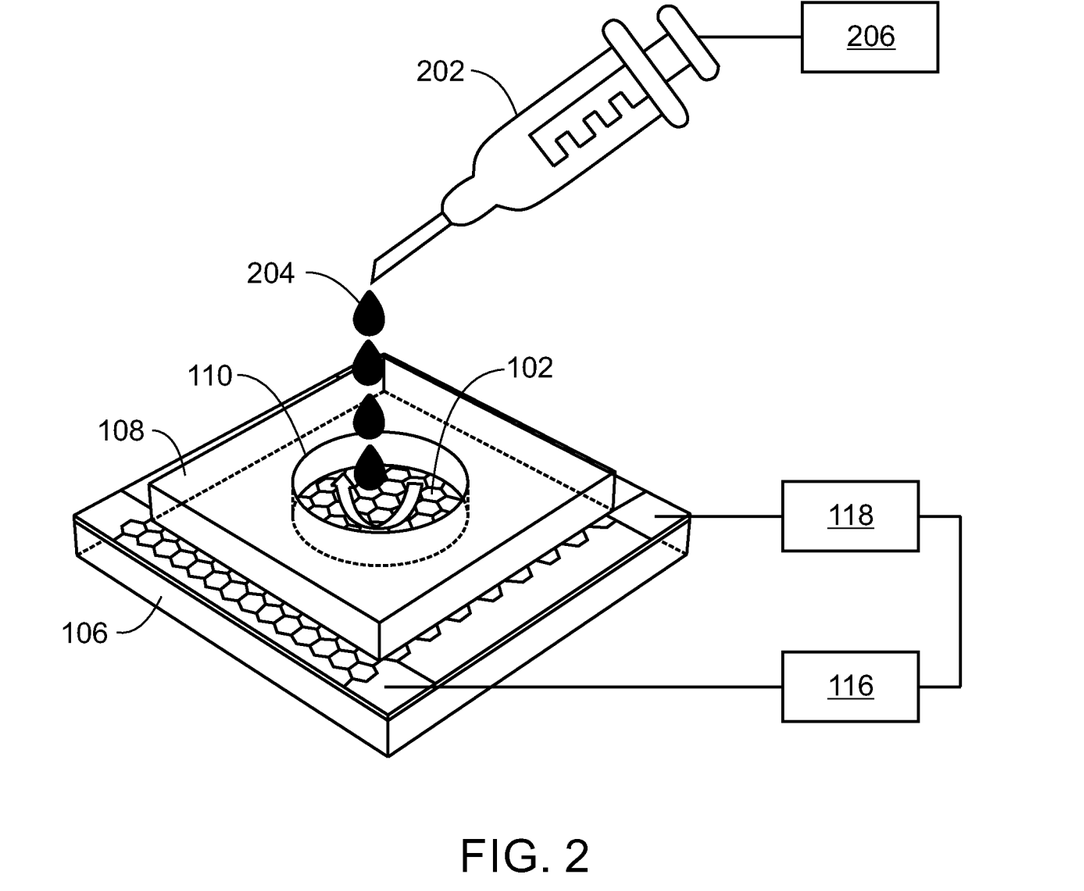
FIG. 2 is a schematic diagram of an example of a first implementation of using the system of FIG. 1.

FIG. 2 is a schematic diagram of an example of a first implementation of using the system of FIG. 1. In this implementation, the lubrication oil sample is dropped onto the COC film 102 of the sensor assembly through the through opening 110 at a rate pre-determined to increase the speed at which any hydrocarbon contaminant in the sample will dissolve/disintegrate the COC film 102. The lubrication oil sample is loaded into a syringe 202 that can hold at least a minimum quantity of the sample needed to be tested using the assembly 100. The syringe 202 can contact the lubrication oil sample with the COC film 102. For example, the syringe 202 can flow drops 204 of the lubrication oil sample onto the COC film 102 through the through opening 110.

In some implementations, the syringe 202 can be loaded onto a syringe pump 206 that can control the flow rate at which the syringe 202 flows the drops 204 of the lubrication oil sample onto the COC film 102. For example, the syringe pump 206 can include or be operatively coupled to a controller. The controller can be implemented as one or more processors and a computer-readable medium (e.g., a non-transitory computer-readable medium) storing instructions which when executed by the one or more processors cause the one or more processors to operate the syringe to flow the lubrication oil sample onto the COC film 102 at a pre-determined flow rate. For example, the pre-determined flow rate can be between 50 microliters per minute and 3 milliliters per minute.

The sensor assembly and the syringe 202 can be spatially arranged at a pre-determined height from which the drops 204 of the lubrication oil sample drop vertically onto the COC film 102. The pre-determined height can range between 1 centimeter and 15 centimeters.

Figure 3:
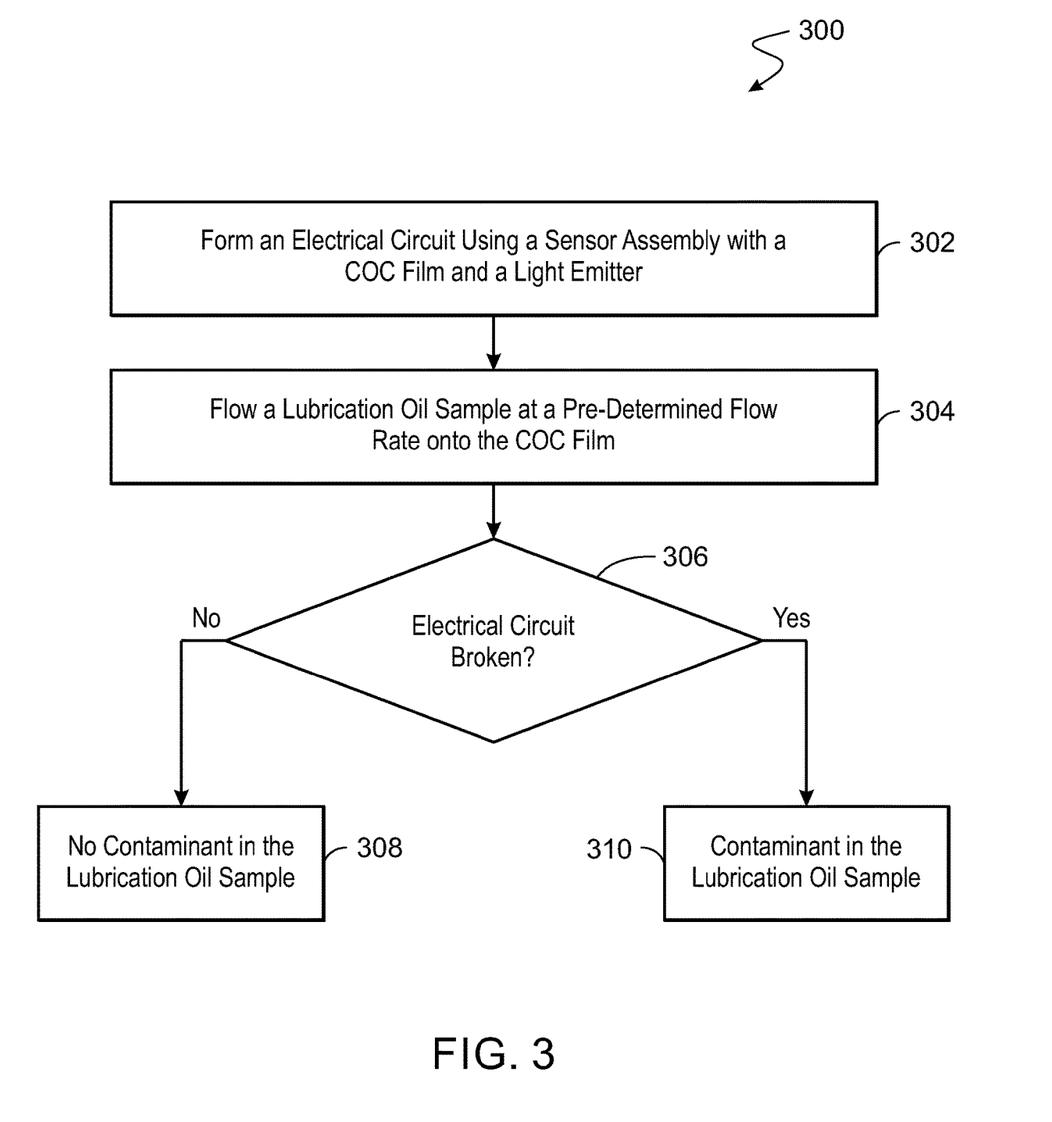
FIG. 3 is a flowchart of an example of a method of using the system of FIG. 1 in the first implementation.

FIG. 3 is a flowchart of an example of a method 300 of using the system 100 in the first implementation. The method 300 can be implemented in part by a human operator and in part by a controller, e.g., the controller of the syringe pump 206 (FIG. 2). At 302, an electrical circuit is formed between a sensor assembly, e.g., the sensor assembly including the COC film 102 (FIG. 1) with the electrically conductive material 104 (FIG. 1) and a light emitter, e.g., the light emitter 118 (FIG. 1). In a default state, the light emitter 118 remains turned on when the electrical circuit is complete and turns off when the electrical circuit is broken. At 304, a lubrication oil sample is flowed at a pre-determined rate onto the COC film 102. For example, drops 204 (FIG. 2) of the lubrication oil sample at dropped at the pre-determined flow rate (e.g., between 50 microliters per minute and 3 milliliters per minute). In some implementations, the drops 204 (FIG. 2) are flowed from a height between 1 centimeter and 15 centimeters directly vertically above the through opening 110 (FIG. 1) of the system 100 (FIG. 1). At 306, a check if performed to determine if the electrical circuit has broken. To do so, a duration of time sufficient for contaminants (if any) in the lubrication oil sample to react with and dissolve/disintegrate the COC film 102 is allowed to pass. If the lubrication oil sample has contaminants, then the electrical circuit breaks and the light emitter 118 turns off. If the lubrication oil sample does not have contaminants, then the electrical circuit does not break and the light emitter 118 remains turned on. If the electrical circuit has not broken (decision branch "NO"), then, at 308, it is determined that the lubrication oil sample is contaminant free. If the electrical circuit has broken (decision branch "YES"), then, at 310, it is determined that the lubrication oil sample is contaminated with the contaminant that can dissolve/disintegrate the COC film 102.

Figure 4:
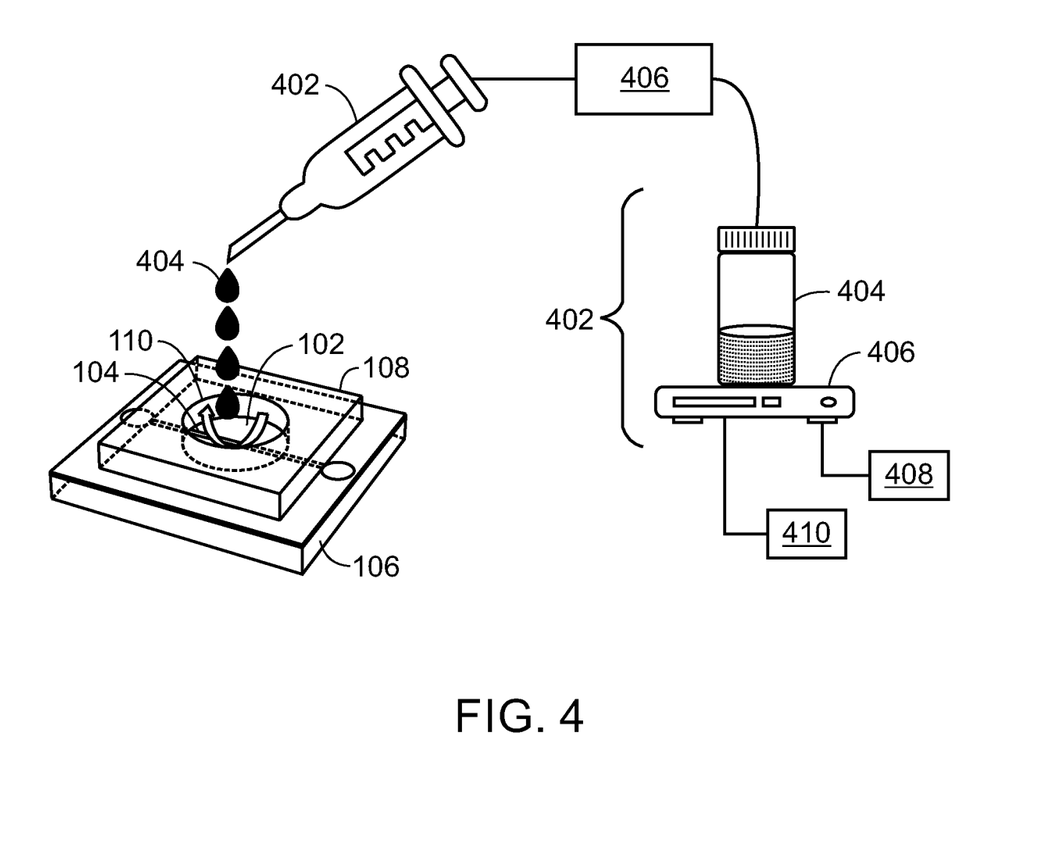
FIG. 4 is a schematic diagram of an example of a second implementation of using the system of FIG. 1.

FIG. 4 is a schematic diagram of an example of a second implementation of using the system of FIG. 1. In this implementation, the lubrication oil sample is heated to a pre-determined temperature optimized to enhance the reaction speed between any hydrocarbon contaminants in the lubrication oil sample and the COC film 102 (FIG. 1). The heated sample can then be dropped onto the COC film 102 of the sensor assembly through the through opening 110 at a pre-determined flow rate as described above with reference to FIGS. 2 and 3.

In some implementations, the system 100 is operatively coupled to a heater assembly 402 that can heat the lubrication oil sample. The heater assembly 402 includes a container 404 to receive the lubrication oil sample. The heater assembly 402 includes a hot plate 404 on which the container 402 is placed to heat the lubrication oil sample. A temperature controller 408 can be coupled to or be built into the hot plate 404. The temperature controller 408 can include or be coupled to a temperature sensor 410 that can sense a temperature of the lubrication oil sample in the container 404. The temperature sensor 410 can transmit the sensed temperature to the temperature controller 408. The temperature controller 408 can control the hot plate 406 based on the temperature sensed by the temperature sensor 410. For example, in response to the temperature sensor 410 determining that the lubrication oil sample has been heated to a pre-determined temperature, the temperature controller 410 can shut down the hot plate 406. The dissolving rate is proportional to applied heat. Consequently, the pre-determined temperature can be any temperature above room temperature, but a threshold temperature (e.g., a few degrees) below the auto ignition temperature of the hydrocarbon mixture at which the hydrocarbon mixture can combust.

The lubrication oil sample, which has been heated to the pre-determined temperature, is loaded into a syringe 402 that can hold at least a minimum quantity of the heated sample needed to be tested using the assembly 100. The syringe 402 can contact the heated lubrication oil sample with the COC film 102. For example, the syringe 402 can flow drops 404 of the lubrication oil sample onto the COC film 102 through the through opening 110.

In some implementations, the syringe 402 can be loaded onto a syringe pump 406 that can control the flow rate at which the syringe 402 flows the drops 404 of the lubrication oil sample onto the COC film 102. For example, the syringe pump 406 can include or be operatively coupled to a controller. The controller can be implemented as one or more processors and a computer-readable medium (e.g., a non-transitory computer-readable medium) storing instructions which when executed by the one or more processors cause the one or more processors to operate the syringe to flow the heated lubrication oil sample onto the COC film 102 at a pre-determined flow rate. For example, the pre-determined flow rate can be between 50 microliters per minute and 3 milliliters per minute.

The sensor assembly and the syringe 402 can be spatially arranged at a pre-determined height from which the drops 404 of the lubrication oil sample drop vertically onto the COC film 102. The pre-determined height can range between 1 centimeter and 15 centimeters.

Figure 5:
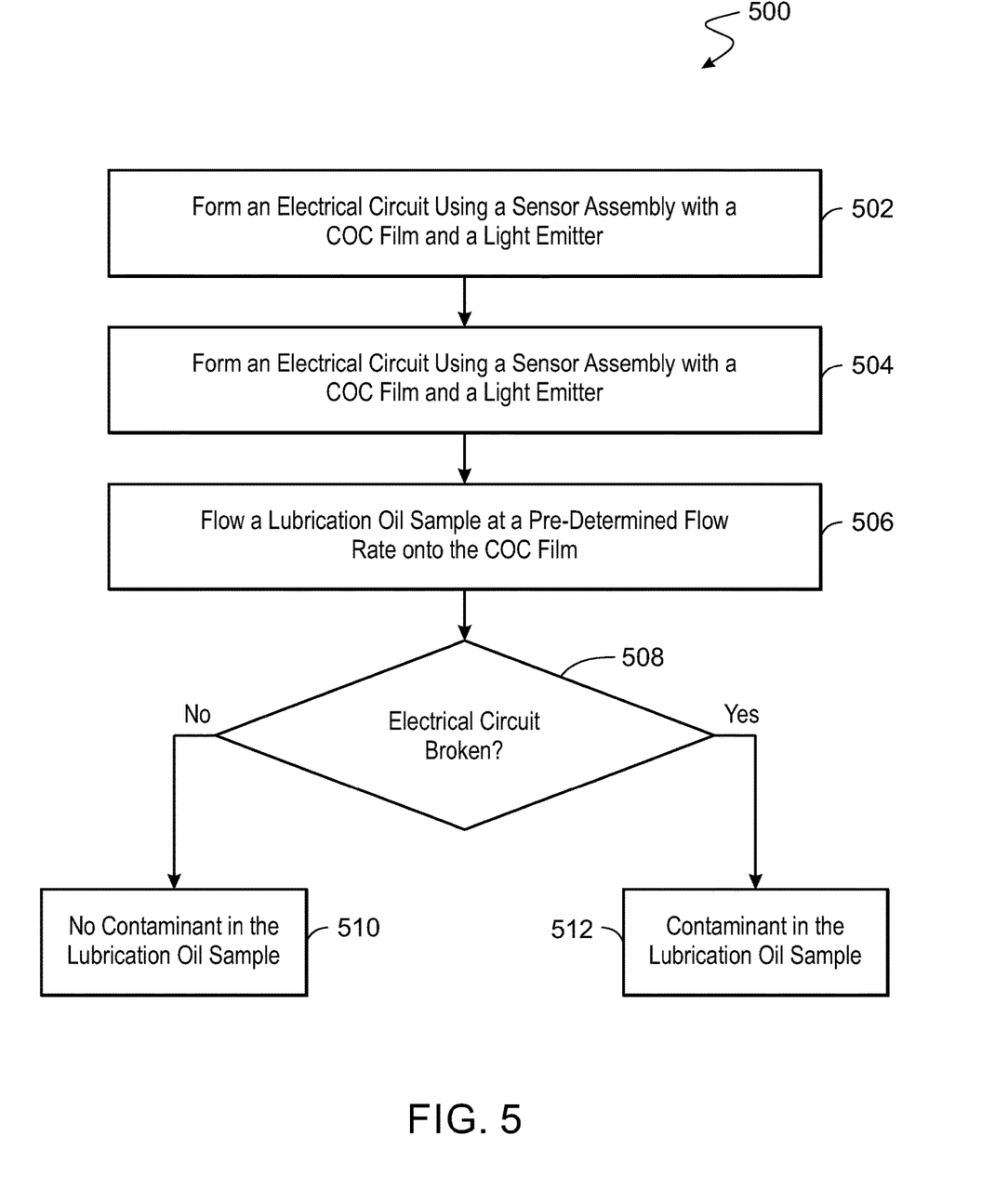
FIG. 5 is a flowchart of an example of a method of using the system of FIG. 1 in the second implementation.

FIG. 5 is a flowchart of an example of a method 500 of using the system 100 in the second implementation. The method 500 can be implemented in part by a human operator and in part by a controller, e.g., the controller of the syringe pump 406 (FIG. 4). At 502, an electrical circuit is formed between a sensor assembly, e.g., the sensor assembly including the COC film 102 (FIG. 1) with the electrically conductive material 104 (FIG. 1) and a light emitter, e.g., the light emitter 118 (FIG. 1). In a default state, the light emitter 118 remains turned on when the electrical circuit is complete and turns off when the electrical circuit is broken. At 504, the lubrication oil sample is heated to a pre-determined temperature, e.g., as described earlier with reference to FIG. 4.

At 506, the heated lubrication oil sample is flowed at a pre-determined rate onto the COC film 102. For example, drops 404 (FIG. 4) of the heated lubrication oil sample at dropped at the pre-determined flow rate (e.g., between 50 microliters per minute and 3 milliliters per minute). In some implementations, the heated drops 404 (FIG. 4) are flowed from a height between 1 centimeter and 15 centimeters directly vertically above the through opening 110 (FIG. 1) of the system 100 (FIG. 1). At 508, a check if performed to determine if the electrical circuit has broken. To do so, a duration of time sufficient for contaminants (if any) in the heated lubrication oil sample to react with and dissolve/disintegrate the COC film 102 is allowed to pass. If the heated lubrication oil sample has contaminants, then the electrical circuit breaks and the light emitter 118 turns off. If the heated lubrication oil sample does not have contaminants, then the electrical circuit does not break and the light emitter 118 remains turned on. If the electrical circuit has not broken (decision branch "NO"), then, at 510, it is determined that the heated lubrication oil sample is contaminant free. If the electrical circuit has broken (decision branch "YES"), then, at 512, it is determined that the heated lubrication oil sample is contaminated with the contaminant that can dissolve/disintegrate the COC film 102.

As described earlier, dropping the sample at an optimized flow rate or heating (or both) the sample speeds up the reaction time between contaminants and the COC film. Such optimization of flow rate or applied heat (or both) also improves sensitivity of the system 100. The dissolving rate of the COC sheet is correlated to the flow rate, COC film thickness and solution temperature. Also, the concentration of the aromatics of the hydrocarbons are correlated to the dissolving rate of the COC film. At pre-known parameters, that dissolving rate gives an indication of the concentration of the aromatics in the mixed solution. At low concentration of aromatics in the solution, the dissolving rate of the film may take longer. For example, to detect 100% of diesel in lubrication oil mixture, only a few seconds may be required. In comparison, to detect 0.5% of diesel in lubrication oil mixture, several hours may be required. By optimizing the flow rate at which the sample is dropped or by heating the sample before dropping onto the system 100, the detection speed, even for low concentrations of contaminant in the sample, can be improved.

Thus, particular implementations of the subject matter have been described. Other implementations are within the scope of the following claims.

The invention claimed is:

1. A hydrocarbon contaminant detection system comprising:
   a sensor assembly comprising a cyclic olefin copolymer (COC) film comprising electrically conductive materials, the sensor assembly configured to complete an electrical circuit, the COC film configured to dissolve in a presence of a hydrocarbon contaminant to cause the electrical circuit to break;
   a syringe configured to carry a lubrication oil sample to be tested using the sensor assembly, the syringe operable to contact the lubrication oil sample with the COC film of the sensor assembly;

a controller comprising:
one or more processors, and
a computer-readable medium storing instructions which when executed by the one or more processors cause the one or more processors to perform operations comprising operating the syringe to flow the lubrication oil sample onto the COC film of the sensor assembly at a pre-determined flowrate.

2. The system of claim 1 further comprising a syringe pump operatively coupled to and controllable by the controller, the syringe pump configured to receive the syringe and to flow the lubrication oil sample in the syringe onto the COC film of the sensor assembly at the pre-determined flowrate.

3. The system of claim 1, wherein the pre-determined flowrate is between 50 microliters per minute and 3 milliliters per minute.

4. The system of claim 1, wherein the sensor assembly and the syringe are spatially arranged at a pre-determined height from which the lubrication oil sample drops vertically onto the COC film.

5. The system of claim 4, wherein the pre-determined height is between 1 centimeter and 15 centimeters.

6. The system of claim 1, wherein the sensor assembly comprises:
a first substrate layer, the COC film positioned on top of the first substrate layer;
a second substrate layer positioned on top of the COC film, the second substrate layer defining a through opening through which the syringe flows the lubrication oil sample onto the COC film between the first substrate layer and the second substrate layer.

7. The system of claim 6, wherein the electrically conductive materials comprise an electrically conductive honeycomb sheet metal positioned below the through opening defined by the second substrate layer.

8. The system of claim 7, wherein a surface area of the first substrate layer is greater than a surface area of the second substrate layer, wherein the sensor assembly comprises electrically conductive metal disposed on portions of the first substrate layer exposed after the second substrate layer is positioned on top of the COC film, wherein the electrically conductive metal contacts the COC film.

9. The system of claim 1, wherein the sensor assembly further comprises a light emitting diode (LED) electrically connected to the COC film, the LED configured to stay on in an absence of the hydrocarbon contaminant and to turn off in a presence of the hydrocarbon contaminant.

10. A method comprising:
forming an electrical circuit between a sensor assembly comprising a cyclic olefin copolymer (COC) film comprising electrically conductive materials and a light emitting diode (LED), wherein the LED remains turned on when the electrical circuit is complete and turns off when the electrical circuit is broken;
flowing a lubrication oil sample at a pre-determined flow rate onto the COC film; and
after flowing the lubrication oil sample at the pre-determined flow rate onto the COC film, detecting that the LED switches off, indicating a presence of a hydrocarbon contaminant in the lubrication oil sample.

11. The method of claim 10, further comprising forming the sensor assembly by:
positioning the COC film on top of a first substrate layer;
forming a through opening through a second substrate layer; and
positioning the second substrate layer over the COC film sandwiching the COC film between the first substrate layer and the second substrate layer.

12. The method of claim 11, further comprising sputtering the electrically conductive materials on the COC film, wherein positioning the second substrate layer over the COC film comprises positioning the electrically conductive materials under the through opening.

13. The method of claim 12, wherein sputtering the electrically conductive materials comprises positioning an electrically conductive honeycomb sheet metal on the COC film.

14. The method of claim 11, wherein a surface area of the first substrate layer is greater than a surface area of the second substrate layer, wherein the method comprises disposing electrically conductive metal on portions of the first substrate layer exposed after the second substrate layer is positioned on top of the COC film such that the electrically conductive metal contacts the COC film.

15. The method of claim 14, wherein the electrically conductive metal is disposed on exposed corners of the first substrate layer.

16. The method of claim 11, wherein flowing the lubrication oil sample at the pre-determined flow rate onto the COC film comprises:
loading the lubrication oil sample into a syringe; and
positioning the syringe directly above the through opening such that the lubrication oil sample drops vertically downward onto the COC film through the through opening.

17. The method of claim 16, wherein the pre-determined flowrate is between 50 microliters per minute and 3 milliliters per minute.

18. The method of claim 17, wherein the pre-determined height is between 1 centimeter and 15 centimeters.

19. The method of claim 16, wherein flowing the lubrication oil sample at the pre-determined flow rate comprises:
loading the syringe onto a syringe pump; and
operating the syringe pump to flow the lubrication oil sample through the syringe at the pre-determined flow rate.

20. A hydrocarbon contaminant detection system comprising:
a sensor assembly comprising a cyclic olefin copolymer (COC) film comprising electrically conductive materials, the COC film sandwiched between a first substrate layer and a second substrate layer with a through opening to access the COC film, electrically conductive materials sputtered on the COC film, the sensor assembly configured to complete an electrical circuit, the COC film configured to dissolve in a presence of a hydrocarbon contaminant to cause the electrical circuit to break;
a syringe configured to carry a lubrication oil sample to be tested using the sensor assembly, the syringe operable to contact the lubrication oil sample with the COC film of the sensor assembly;
a syringe pump configured to receive the syringe carrying the lubrication oil sample, the syringe pump configured to drive the syringe to flow the lubrication oil sample onto the COC film of the sensor assembly at a pre-determined flowrate, wherein a break in the electrical circuit responsive to the lubrication oil sample being flowed onto the COC film indicates a presence of a hydrocarbon contaminant in the lubrication oil sample.

* * * * *